United States Patent [19]
Khalil et al.

[11] Patent Number: 5,747,806
[45] Date of Patent: May 5, 1998

[54] METHOD AND APPARATUS FOR MULTI-SPECTRAL ANALYSIS IN NONINVASIVE NIR SPECTROSCOPY

[75] Inventors: Gamal Khalil, Chandler, Ariz.; Stephen F. Malin, Chanhassen, Minn.

[73] Assignee: Instrumentation Metrics, Inc, Tempe, Ariz.

[21] Appl. No.: 596,409

[22] Filed: Feb. 2, 1996

[51] Int. Cl.$^6$ .................................................. G01N 21/35
[52] U.S. Cl. .................. 250/339.12; 250/339.09; 250/339.11; 250/341.8
[58] Field of Search .............. 250/339.12, 341.8, 250/339.11, 339.09

[56] References Cited

U.S. PATENT DOCUMENTS

| | | |
|---|---|---|
| 3,821,550 | 6/1974 | Priest . |
| 3,822,098 | 7/1974 | Rudder er al. .................... 356/209 |
| 4,306,152 | 12/1981 | Ross et al. . |
| 4,427,889 | 1/1984 | Müller . |
| 4,655,225 | 4/1987 | Dähne et al. . |
| 4,738,535 | 4/1988 | Webster . |
| 4,805,623 | 2/1989 | Jobsis . |
| 4,882,492 | 11/1989 | Schlager . |
| 4,883,953 | 11/1989 | Koashi et al. . |
| 4,975,581 | 12/1990 | Robinson et al. . |
| 5,023,804 | 6/1991 | Hoult . |
| 5,054,487 | 10/1991 | Clarke . |
| 5,086,229 | 2/1992 | Rosenthal et al. . |
| 5,099,123 | 3/1992 | Harjunmaa ............... 250/345 |
| 5,121,337 | 6/1992 | Brown . |
| 5,146,091 | 9/1992 | Knudson . |
| 5,209,231 | 5/1993 | Cote et al. . |
| 5,222,495 | 6/1993 | Clarke et al. . |
| 5,222,496 | 6/1993 | Clarke et al. . |
| 5,242,602 | 9/1993 | Richardson et al. . |
| 5,252,829 | 10/1993 | Nygaard et al. . |
| 5,267,152 | 11/1993 | Yang et al. . |
| 5,321,970 | 6/1994 | Davies et al. ............... 73/1 R |
| 5,355,880 | 10/1994 | Thomas et al. . |
| 5,360,004 | 11/1994 | Purdy et al. . |
| 5,370,114 | 12/1994 | Wong et al. . |
| 5,406,082 | 4/1995 | Pearson et al. ............. 250/339.01 |
| 5,459,317 | 10/1995 | Small et al. . |
| 5,500,530 | 3/1996 | Gregoris ..................... 250/339.11 |

FOREIGN PATENT DOCUMENTS

| | | |
|---|---|---|
| 0 426 358 A1 | 5/1991 | European Pat. Off. . |
| 0 631 137 A2 | 12/1994 | European Pat. Off. . |
| 0 670 143 A1 | 6/1995 | European Pat. Off. . |
| 0 757 243 A1 | 12/1995 | European Pat. Off. . |
| WO 91/11136 | 8/1991 | WIPO . |
| WO 92/17765 | 10/1992 | WIPO . |

OTHER PUBLICATIONS

SBIR, Phase I, Monthly Technical Progress Report No. 1, Near Infrared Spectral Determination of Human Tissue pH, Contract No.: DAMD 17–95–C–5035, Biotronics Technologies, Inc., Mar. 15–Apr. 15, 1995 (Apr. 23, 1995).

SBIR, Phase I, Monthly Technical Progress Report No. 2, Near Infrared Spectral Determination of Human Tissue pH, Contract No.: DAMD 17–95–C–5035, Biotronics Technologies, Inc., Apr. 15–May 15, 1995 (May 18, 1995).

Small Business Innovation Research (SBIR) Program, Topic No. A94–080, Near Infrared Spectral Determination of Human Tissue pH, Biotronics Technologies, Inc., Jul. 14, 1994.

(List continued on next page.)

*Primary Examiner*—Constantine Hannaher
*Attorney, Agent, or Firm*—Bozicevic & Reed LLP

[57] ABSTRACT

The concentration of an analyte present in a sample is determined using multi-spectral analysis in the near infrared range. Incident radiation containing a plurality of distinct, nonoverlapping regions of wavelengths in the range of approximately 1100 to 3500 nm is used to scan the sample. Diffusively reflected radiation emerging from the sample is detected, and a value indicative of the concentration of the analyte is obtained using an application of chemometrics techniques. Information obtained from each nonoverlapping region of wavelengths can be cross-correlated to remove background interferences.

23 Claims, 4 Drawing Sheets

OTHER PUBLICATIONS

Award/Contract No. DAMD 17–95–C 5035 dated Mar. 15, 1995, Requisition/Purchase Request/Project No. FORM92–9421–4010, issued by U.S. Army Medical Research Acquisition Activity to contractor Biotronics Technologies Inc.

U.S. Appl. No. 08/547145, Oct. 24, 1995, Schlager.

N.M. Faber et al., "Generalized Rank Annihilation Method. III: Practical Implementation", *Jrn. of Chemometrics* 8:273–285 (1994).

H.M. Heise et al., "Noninvasive Blood Glucose Sensors Based on Near–Infrared Spectroscopy", *Blackwell Scientific Pub., Inc.* 18(6):439–447 (1994).

Walter Lindberg et al; "Multivariate Resolution of Overlapped Peaks in Liquid Chromatography Using Diode Array Detection", *Anal. Chem.* 58:299–303 (1986).

Lois A. Marquardt et al., "Near–Infrared Spectroscopic Measurement of Gluycose in a Protein Matrix" *Anal. Chem.* 65:3271–3278 (1993).

H. Zeller et al., "Blood Glucose Measurement by Infrared Spectroscopy", *Blackwell Scientific Pub., Inc.* 12(2):129–135 (1989).

METHOD AND APPARATUS FOR MULTI-SPECTRAL ANALYSIS IN NONINVASIVE NIR SPECTROSCOPY

TECHNICAL FIELD

The present invention relates to a method and apparatus for determining the concentration of a target analyte in a sample using multi-spectral analysis. The invention finds application in a wide range of chemical analyses, particularly in noninvasive spectrophotometric analysis of blood analytes.

BACKGROUND OF THE INVENTION

The measurement of the concentration of blood constituents finds application in a variety of procedures for the diagnosis and treatment of conditions and disease in human subjects. One important application is in the measurement of blood glucose. Specifically, the concentration of blood glucose should be monitored on a periodic basis in persons suffering from diabetes, and in insulin-dependent or Type I diabetes, it is often necessary or desirable to monitor blood glucose several times a day. Further, the measurement of blood cholesterol concentrations provides important information in the treatment or prevention of persons suffering from coronary artery disease, and the measurement of other organic blood analytes, such as bilirubin and alcohol, is important in various diagnostic contexts.

The most accurate and widely practiced method of obtaining blood analyte concentrations involves the extraction of blood from a patient, which blood is then analyzed, either in a laboratory using highly accurate and sensitive assay techniques, or by the use less accurate self-testing methods. In particular, traditional blood glucose monitoring methods require the diabetic to draw a blood sample (e.g., by a finger-tip lance) for each test and to read the glucose level using a glucometer (a spectrophotometer that reads glucose concentrations) or a calorimetric calibration method. Such invasive blood extractions create a painful and tedious burden to the diabetic and expose the diabetic to the possibility of infection, particularly in light of the frequency of testing which is necessary. These considerations can lead to an abatement of the monitoring process by the diabetic.

Accordingly, there is a recognized need in the art for a simple and accurate method and device for noninvasively measuring blood analyte concentration, particularly in the context of blood glucose monitoring by diabetics. One approach to the problem involves the use of traditional methods of near infrared (near-IR) analysis, wherein the measurement of absorbance at one or more specific wavelengths is used to extract analyte-specific information from a given sample.

Near-IR absorbance spectra of liquid samples contain a large amount of information about the various organic constituents of the sample. Specifically, the vibrational, rotational and stretching energy associated with organic molecular structures (e.g., carbon—carbon, carbon-hydrogen, carbon-nitrogen and nitrogen-hydrogen chemical bonds) produces perturbations in the near-IR region which can be detected and related to the concentration of various organic constituents present in the sample. However, in complex sample matrices, near-IR spectra also contain an appreciable amount of interferences, due in part to similarities of structure amongst analytes, relative levels of analyte concentration, interfering relationships between analytes and the magnitude of electronic and chemical "noise" inherent in a particular system. Such interferences reduce the efficiency and precision of measurements obtained using near-IR spectrometry to determine the concentration of liquid sample analytes. However, a number of near-IR devices and methods have been described to provide noninvasive blood analyte determinations.

U.S. Pat. No. 5,360,004 to Purdy et al. describes a method and apparatus for the determination of blood analyte concentrations, wherein a body portion is irradiated with radiation containing two or more distinct bands of continuous-wavelength incident radiation. Purdy et al. emphasize filtration techniques to specifically block radiation at the two peaks in the NIR absorption spectrum for water, occurring at about 1440 and 1935 nm. Such selective blocking is carried out in order to avoid a heating effect that may be due to the absorption of radiation by water in the body part being irradiated.

By contrast, U.S. Pat. No. 5,267,152 to Yang et al. describes noninvasive devices and techniques for measuring blood glucose concentration using only the portion of the IR spectrum which contains the NIR water absorption peaks (e.g., the "water transmission window," which includes those wavelengths between 1300 and 1900 nm). Optically controlled light is directed to a tissue source and then collected by an integrating sphere. The collected light is analyzed and blood glucose concentration calculated using a stored reference calibration curve.

Devices have also been described for use in determination of analyte concentrations in complex samples.

For example, U.S. Pat. No. 5,242,602 to Richardson et al. describes methods for analyzing aqueous systems to detect multiple active or inactive water treating components. The methods involve determination of the absorbance or emission spectrum of the components over the range of 200 to 2500 nm, and application of chemometrics algorithms to extract segments of the spectral data obtained to quantify multiple performance indicators.

U.S. Pat. No. 5,252,829 to Nygaard et al. describes a method and apparatus for measuring the concentration of urea in a milk sample using an infrared attenuation measuring technique. Multivariate techniques are carried out to determine spectral contributions of known components using partial least squares algorithms, principal component regression, multiple linear regression or artificial neural network learning. Calibration is carried out by accounting for the component contributions that block the analyte signal of interest. Thus, Nygaard et al. describe a technique of measuring multiple analyte infrared attenuations and compensating for the influence of background analytes to obtain a more accurate measurement.

U.S. Pat. No. 4,975,581 to Robinson et al. describes a method and apparatus for determining analyte concentration in a biological sample based on a comparison of infrared energy absorption (i.e., differences in absorption at several wavelengths) between a known analyte concentration and a sample. The comparison is performed using partial least squares analysis or other multivariate techniques.

U.S. Pat. No. 4,882,492 to Schlager describes a method and apparatus for non-invasive determination of blood analyte concentrations. Modulated IR radiation is directed against a tissue sample (e.g., an ear lobe) and either passed through the tissue or impinged on a skin surface where it is spectrally modified by a target analyte (glucose). The spectrally modified radiation is then split, wherein one portion is directed through a negative correlation cell and another through a reference cell. Intensity of the radiation passing through the cells are compared to determine analyte concentration in the sample.

U.S. Pat. No. 4,306,152 to Ross et al. describes an optical fluid analyzer designed to minimize the effect of background absorption (i.e., the overall or base level optical absorption of the fluid sample) on the accuracy of measurement in a turbid sample or in a liquid sample which is otherwise difficult to analyze. The apparatus measures an optical signal at the characteristic optical absorption of a sample component of interest and another signal at a wavelength selected to approximate background absorption, and then subtracts to reduce the background component of the analyte-dependent signal.

The accuracy of information obtained using the above-described methods and devices is limited by the spectral interference caused by background, i.e., non-analyte, sample constituents that also have absorption spectra in the near-IR range. Appreciable levels of background noise represent an inherent system limitation, particularly when very little analyte is present. In light of this limitation, attempts have been made to improve signal-to-noise ratios, e.g., by avoiding water absorption peaks to enable the use of increased radiation intensity, by reducing the amount of spectral information to be analyzed, or by using subtraction or compensation techniques based on an approximation of background absorption. Although such techniques have provided some improvement, there remains a need to provide a method and apparatus capable of rendering a more precise determination of the concentration of analytes in a liquid matrix, particularly in the context of blood glucose monitoring.

SUMMARY OF THE INVENTION

Accordingly, it is a primary object of the invention to address the above-described needs in the art, by providing a method of determining the concentration of an analyte present in a sample having a varying background matrix and possibly having substantial component interferences as well. The method accounts for the similarity of structures among various components present in the sample, the relative magnitude of the analyte concentration and spectral interferences provided by various sample components and instrumentation variances.

The method generally involves: (1) identifying several distinct, nonoverlapping regions of wavelengths in the range of approximately 1100 to 3500 nm which have high correlation to the concentration of the analyte; (2) irradiating a sample with incident radiation containing those regions in order to obtain radiation that has been spectrally attenuated as a result of interaction with sample constituents; (3) detecting the spectrally attenuated radiation; (4) measuring the intensity of the spectrally attenuated radiation at a wavelength in nonoverlapping regions of wavelengths; and (5) correlating the measurements to obtain a value indicative of the concentration of the analyte.

It is also an object of the invention to provide a spectrophotometric apparatus for determining the concentration of an analyte present in a sample having a varying background matrix and substantial component interferences. The apparatus is used in a multi-spectral analysis to obtain spectral information containing analyte-specific signals as well as signals related to instrument background noise and interfering spectral information. Chemometrics techniques are used to configure filter elements capable of enhancing the correlation of analyte-specific information with the concentration of the analyte and to derive system algorithms capable of determining analyte concentration values.

In one aspect of the invention, an apparatus is provided which includes a specialized optical transfer cell that is capable of enhancing the correlation of analyte-specific information with the concentration of the analyte. The specialized optical transfer cell contains a positive correlation filter adapted to selectively emphasize wavelengths having high correlation with the concentration of a selected analyte. The emphasized wavelengths are communicated to a means for receiving the information and converting the same into a signal representative of the intensity of the wavelength.

DETAILED DESCRIPTION OF THE PREFERRED EMBODIMENTS

Before the invention is described in detail, it is to be understood that this invention is not limited to the particular component parts of the devices or methods described, as such may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "an optical transfer cell" includes two or more optical transfer cells, "a means for reflectively transmitting radiation" includes two or more such means, "a wavelength" includes two or more wavelengths, "a chemometrics algorithm" includes two or more algorithms, and the like.

In this specification and in the claims which follow, reference will be made to a number of terms which shall be defined to have the following meanings:

"Chemometrics" relates to the application of mathematical, statistical and pattern recognition techniques in chemical analysis applications. See, e.g., Brown et al. (1990) *Anal. Chem.* 62:84–101. Chemometrics is practiced herein in the context of developing and using noninvasive diagnostic instrumentation that employs advanced signal processing and calibration techniques. Signal processing is used to improve the accessibility of physically significant information in analytical signals. Examples of signal processing techniques include Fourier transformation, first and second derivatives, and digital or adaptive filtering.

In the context of chemometrics, "calibration" refers to the process of relating data measurements to a chemical concentration for the purpose of quantification. Particularly, statistical calibrations using chemometric methods can be used to extract specific information from a complex set of data. Such methods of calibration include linear regression, multiple-linear regression, partial linear regression, and principal components analysis. In other applications, calibrations can be carried out using artificial neural networks, genetic algorithms and rotated principal components analysis.

Instrumentation that detects information for one or more constituents in a complex chemical matrix must rely upon analysis algorithms (such as those derived using chemometrics) in order to reveal information that is specific for one or more chemical constituent. Chemometrics techniques can be used to compare unknowns with calibrated standards and data bases to provide advanced forms of cluster analysis, and to extract features from an unknown sample that can be used as information in statistical and mathematical models.

"Principal components analysis" (PCA) is one method of data reduction which can be performed in the application of chemometric techniques to spectroscopic measurement of chemical analytes in a complex matrix. PCA is used to reduce the dimensionality of a large number of interrelated variables while retaining the information that distinguishes one component from another. This reduction is effected using an eigenvector transformation of an original set of interrelated variables (e.g., an absorption spectrum) into a substantially smaller set of uncorrelated principal component (PC) variables that represents most of the information in the original set. The new set of variables is ordered such that the first few retain most of the variation present in all of the original variables. See, e.g., Jolliffe, L. T., *Principal Component Analysis,* Sprinter-Verlag, New York (1986). More particularly, each PC is a linear combination of all the original measurement variables. The first is a vector in the direction of the greatest variance of the observed variables. The succeeding PCs are chosen to represent the greatest variation of the measurement data and to be orthogonal to the previously calculated PC. Therefore, the PCs are arranged in descending order of importance.

The term "weighting constant" includes the wavelength coefficients of partial least squares regression and/or principal components regression, or any constant obtained from any statistical calibration that can be used to calculate values (such as analyte concentration) for unknown samples. A "wavelength weighting factor" is an embodiment of a weighting constant which is used in the construction of an optical filter means capable of emphasizing wavelength-specific information from spectral data. The wavelength-specific information can be used to determine desired values relating to the sample undergoing analysis (e.g., analyte concentration). A wavelength weighting factor can be embodied as a particular filter density (e.g., neutral or wavelength-specific), filter thickness, or the like, such parameters having been determined using the above-described statistical calibration techniques.

The term "optical transfer cell" encompasses any optically active element that partially absorbs incident radiation in the visible, ultraviolet, or infrared spectral regions, wherein the partial absorption is selective with respect to wavelength. For the purposes of the present invention, an optical transfer cell generally comprises an optical filter means having absorption characteristics that were derived from a partial least squares or principal components regression analysis. The optical filter means is used to selectively emphasize wavelengths having high correlation with a selected analyte concentration. "High correlation," or "close correlation" refers to the quantitative association between the absorption spectrum at a particular wavelength and a particular analyte concentration, wherein the two variables have a correlation coefficient (r) of 0.9 or higher.

A "positive correlation filter" is an optical filter means having an absorption spectrum sufficient to emphasize radiation of particular wavelengths corresponding to the target analyte and not to other absorbing analytes. Thus, the positive correlation filter provides an optimal transfer function that is highly correlated with the analyte concentration in the sample being measured. An ideal positive correlation filter would correlate perfectly with a target analyte (i.e., the correlation coefficient r would be +1.0), and not correlate at all with all other interfering absorbing analytes in a particular sample (r would be 0.0). The synthesis of positive correlation filters is carried out herein using chemometric techniques to determine appropriate wavelength weighting factors.

A "neutral density filter" refers to a standard optical filter means having a flat absorption spectrum. A neutral density filter can be used in concert with correlation filters in a filter system to provide a weighting factor to attenuate absorbances due to the analyte at selected wavelengths and further improve the accuracy of the correlation provided by the system. A neutral density filter can have an absorption spectrum sufficient to attenuate radiation equally at all wavelengths in the range of interest.

As used herein, an "aqueous medium" encompasses any substrate relating to, made from, or comprising water. Thus, an aqueous medium includes media wherein water is the major component, i.e., is present in an amount of at least about 50%, as well as wherein water is a solvent but is present in amounts of less than about 50%. Aqueous mediums are specifically defined herein to include mammalian tissue.

The term "blood analyte" refers to a blood constituent that is absorbing in the near-IR range, the measurement of which is useful in patient monitoring or in the provision of health care.

As used herein, the term "near infrared" or "near-IR" encompasses radiation in a spectrum ranging from about 660 to about 3500 nm, more preferably from about 1050 to about 2850 nm, and most preferably from about 1100 to about 2500 nm.

The term "background absorption" relates to the overall or base level of optical absorption of an aqueous sample which is to be analyzed, from which the absorption of a selected constituent departs at one or more characteristic wavelengths to an extent indicative of the concentration of the selected constituent. When the level of background absorption is high in relation to the characteristic absorption of the selected constituent, such as in complex aqueous media where numerous interfering constituents are found, accurate measurement of the magnitude of a slight change in the absorption at the characteristic wavelength of a constituent of interest requires application of the chemometrics techniques described herein. This is particularly so in applications wherein the overall concentration of the constituent of interest is low relative to the aqueous medium, e.g., in the measurement of blood analytes.

General Methods

A spectrophotometric method is provided for determining the concentration of an analyte in a liquid sample using near-IR radiation. In contrast to prior techniques, the present method uses all of the spectral information contained in the near-IR region in order to obtain a set of measurements that can be used to determine an analyte concentration with a heightened degree of accuracy.

The method includes the steps of (1) selecting several distinct, nonoverlapping regions of wavelengths from the near-IR range spanning 1100–3500 nm, wherein each region defines a spectral range, (2) irradiating a sample using near-IR light containing the selected spectral ranges to obtain spectrally modified radiation which has been attenuated, (3) collecting and measuring the intensity of the spectrally-attenuated radiation at one or more wavelengths contained within each of the selected spectral ranges, and (4) correlating those measurements to obtain a value indicative of analyte concentration.

Spectral information obtained using this method can be subjected to a combination of mathematical transformations to arrive at a precise analyte concentration value. For example, standard statistical techniques, such as partial least squares (PLS) analysis, or principal components regression (PCR) analysis, can be used to correlate the absorbance of radiation at specific wavelengths to analyte structure and concentration. PLS techniques are described, for example, in Geladi et al. (1986) *Analytica Chimica Acta* 185:1–17. For a description of PCR techniques, reference may be had to Jolliffe, L. T., *Principal Component Analysis,* Sprinter-Verlag, New York (1986).

Accordingly, in determining blood analyte concentration from a body tissue sample, one method involves the selection of three nonoverlapping regions of wavelengths from the near IR range spanning 1100 to 3500 nm; specifically, a first region spanning 1100 to 1350 nm, a second region spanning 1430 to 1450 nm or 1930 to 1950 nm, and a third region spanning 2000 to 2500 nm, wherein each region defines a "spectral range." The first region contains wavelengths in which proteins and other cellular components exhibit dominant spectral activity, the second region is dominated by the absorption spectrum of water, and the third region contains wavelengths in which organic analyte molecules exhibit significant spectral activity. These constituents also contribute to the absorption spectra in those regions where they are not the dominant species. Accordingly, the spectrally attenuated radiation obtained from each region contains a large amount of interrelated information that must be reduced using statistical methods to obtain analyte-specific information.

The invention also involves the use of signal processing to improve the accessibility of physically significant information in the analytical signals. The intensity values of signals obtained at particular wavelengths can thus be processed to reduce the effect of instrumentation noise. The processed signals are then subjected to multivariate analysis using known statistical techniques.

The PCA method of data reduction is one preferred method used in the practice of the invention to reduce the dimensionality of a large number of interrelated variables while retaining information that distinguishes one component from another. Data reduction is carried out using an eigenvector transformation of an original set of interrelated variables (e.g., the absorption spectrum) into a substantially smaller set of uncorrelated principal component (PC) variables that represents most of the information in the original set. The new set of variables is ordered such that the first few retain most of the variation present in the original set.

The principal component vectors can be transformed by orthogonal rotation against an average value for the absorbance to obtain both a known wavelength and the relative value of the absorbance at that wavelength which is attributable to the analyte. By performing this analysis on information obtained from each of the three spectral regions, cross-correlating the principal component vectors via a linear algorithm, and using subtractive methods to remove the effect of interfering analytes, values are obtained which can be used in a system algorithm to determine the concentration of the analyte.

Multivariate techniques are used to provide a model that relates the intensity of radiation at specific wavelengths in each spectral region to analyte concentrations in a particular sample matrix, e.g., body tissue. The model is constructed using two sets of exemplary measurements that are obtained simultaneously, the first set of measurements, the "prediction set," comprising spectral data, e.g., radiation intensity at selected wavelengths, and the second set of measurements, the "calibration set," comprising highly accurate analyte concentrations that have been determined using invasive sampling techniques. The procedure is carried out over a range of analyte concentrations to provide calibration and prediction data sets.

Measurements obtained in both the calibration set and the prediction set are subjected to multivariate analysis, such as by the use of commercially available multivariate model developing software programs, to provide an initial model. The initial model is applied to the prediction data to derive analyte concentration values that can be compared to the values obtained by the invasive techniques. By iteratively performing the above steps, a refined model is developed which can be used to establish a system algorithm for use in analyzing data obtained by the methods of the invention.

The above-described multivariate techniques can also be used to design an optically active element capable of enhancing correlation of spectral information with analyte concentration, e.g., a positive correlation filter system. Particularly, the solutions obtained using multivariate analysis can be used to determine optical parameters, such as absorption characteristics, for positive correlation filter systems.

In the practice of the invention, non-analyte specific information from the various nonoverlapping spectral regions is also used, for example, to normalize each spectral scan, to subtract background and base line interferences, or to provide signal values used to detect an inaccurate measurement.

When determining a blood analyte concentration in a body tissue sample, measurements taken in the spectral range spanning approximately 1320–1340 nm provide a highly reflected, unattenuated, signal, as there are no major absorption bands present in the region. By collecting and measuring the intensity of radiation in that range, a value is obtained which can be used to estimate the actual intensity of the near-IR light used to irradiate the sample. The value can be used to normalize each individual scan and to correct for fluctuations in the intensity of the light source which could effect the accuracy of analyte concentration values obtained using the method of the invention.

Additionally, measurements taken in the spectral ranges spanning approximately 1430–1450 nm and approximately 1930–1950 nm provide substantially nonreflected, highly attenuated, signals, as a result of the two dominant absorption peaks occurring at about 1440 and 1935 nm in the near-IR absorption spectrum for water. By collecting and measuring the intensity of radiation in one or both of those ranges, a value is obtained which can be used to estimate the intensity of near-IR light that is not totally absorbed by the irradiated sample. The value can be used to subtract background or base-line information from the analyte-specific signals obtained in other regions and/or to provide an internal reference to detect inaccurate measurements. The value can be subtracted from each spectral measurement obtained using the present method in order to correct for the pedestal effect caused by specular reflection which varies with skin texture and age.

Measurements of substantially unattenuated signals obtained from a first region (e.g., the spectral range spanning approximately 1320–1340 nm) and measurements of highly attenuated signals obtained from a second region (e.g., the spectral ranges spanning approximately 1430–1450 nm and approximately 1930–1950 nm) can also be used to compare diffusely reflected radiation with specular radiation. If the signals in the two regions have relatively comparable values, it is likely that most of the radiation used to irradiate the tissue sample was reflected from the skin surface, and thus failed to penetrate the skin to interact with the blood analytes. This information can be used to identify ineffective measurements arising from a failure to obtain a proper instrumentation scan of the tissue sample.

Figure 1:
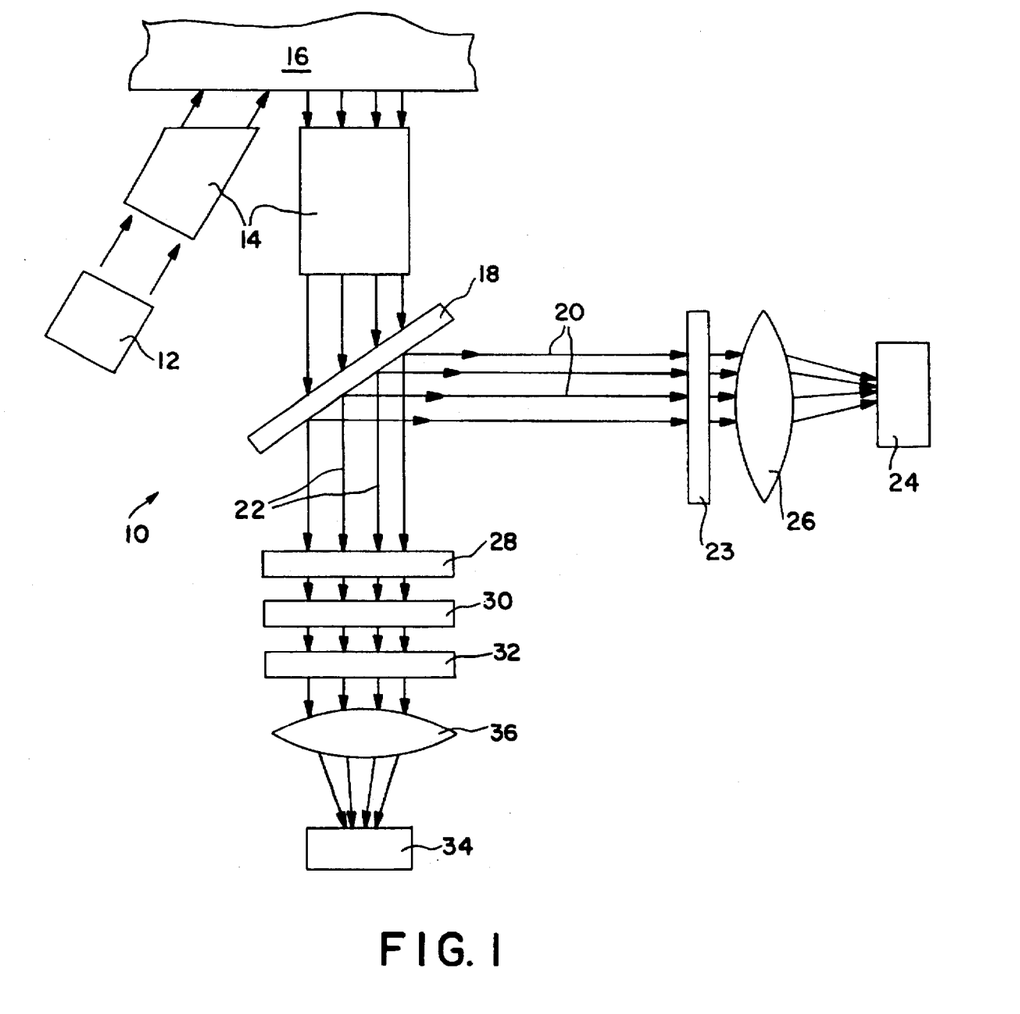
FIG. 1 is a diagrammatic representation of an apparatus constructed according to the invention.

The method of the invention can be carried out using a number of spectrophotometer configurations. Referring now to FIG. 1, one particular apparatus for determining the concentration of an analyte in a liquid sample is generally indicated at 10. The apparatus includes a radiation source 12 which provides a plurality of distinct, nonoverlapping regions of wavelengths in the approximate range of 600 to approximately 3500 nm. A number of suitable radiation sources are known in the art, such as incandescent light sources directed across interference filters, halogen light sources, modulated by an associated chopper wheel, laser light sources, laserdiode arrays, or high speed light-emitting diode (LED) arrays. In one particular apparatus, the radiation source 12 provides radiation at three distinct regions of wavelengths, specifically a first region of wavelengths in the approximate range of 1100 to 1350 nm, a second region in the approximate range of 1930 to 1950 nm and a third region in the approximate range of 2000 to 3500 nm.

The apparatus 10 also includes sample interface optic means 14 which launches incident radiation from the radiation source into contact with a sample medium 16 containing an analyte. After contacting the sample medium, spectrally modified radiation emerging from the sample as diffusively reflected light is collected and delivered to a first lens system 18, whereby the light is directed into first and second light paths, respectively indicated at 20 and 22. The first lens system 18 can comprise a partial reflected mirror configuration such as those known in the art.

In various configurations, the sample interface optic means 14 can be designed to enable the close interface of the apparatus 10 with the medium 16, such as where the launch is carried out by placing the apparatus in direct contact with the sample medium, thereby bringing the radiation source into close proximity with the sample to be analyzed. After the launch, the reflected radiation is collected using optically active means, such as light converging means or beam deflection optics. Alternatively, the sample interface optic means 14 can comprise fiber optic waveguides coupled to the apparatus in order to enable remote apparatus placement and operation. Other configurations are provided wherein a single fiber optic bundle is employed to transmit the radiation to and from the medium. An optrode disposed at the end of the single bundle transmits the near-IR radiation to the sample medium 16 and receives spectrally modified radiation therefrom which is directed back through the bundle to the apparatus 10. Sapphire or high-grade quartz can be used as optical elements in the above fiber optic waveguides, as those materials have very good transmission characteristics in the near-IR spectral range.

The reflected light in the first light path 20 is communicated with a first filter means 23 which has been configured to pass specific wavelengths of light which are independent of any analyte concentration. In one configuration, the first filter means can comprise a narrow band-pass filter which has near-IR absorption characteristics that selectively pass a region of radiation containing wavelengths with substantially no correlation with the concentration of the analyte. Radiation emerging from the first filter means 23 is then communicated to a first detection means 24. Communication of the radiation to the first detection means can be carried out via a focusing means 26, e.g., a collimating lens or the like. Alternatively, the apparatus 10 can include a radiation detector that is capable of directly receiving radiation from the first filter means.

The first detection means detects and converts the passed radiation into a signal that is representative of the intensity of the analyte-independent radiation. In one particular apparatus, the first detection means 24 comprises a lead sulfide photodetector that is able to scan the range of wavelengths from about 1100 to at least about 3500 nm in steps of 1 nm.

Signals obtained from the first detection means can be readily converted into digital signals, e.g, digital signals indicative of the intensity of the analyte-independent wavelengths, using an analog/digital converter. The digitized information is readily available for input into a microprocessor or other electronic memory means, such as those known in the art.

Referring still to FIG. 1, the reflected light in the second light path 22 is passed to an adjustable filter means 28 which is capable of having its absorption characteristics adjusted in response to a signal that is either externally generated, or that has been generated by the apparatus 10. The adjustable filter means generally comprises a screen filter, such as a neutral density filter, having absorption characteristics that are adjusted to variably attenuate the intensity of radiation as dictated by an external signal or system command. The degree of attenuation provided by the adjustable filter means 28 is based upon a predetermined factor selected to ensure that radiation emitted from the adjustable filter will be at a constant value regardless of the intensity of the pre-filtered radiation. In one particular apparatus, the attenuation provided by the adjustable filter means is regulated by a feedback signal generated by the first detection means 24.

Attenuated radiation emerging from the adjustable filter means 28 is communicated to a principal analyte filter 30 which has optical characteristics capable of selectively passing one or more wavelengths from each of the distinct nonoverlaping regions of wavelengths launched by the radiation source 12. The wavelengths passed by the principal analyte filter are selected to have a correlation with the concentration of the analyte.

A second filter means 32 is arranged in the apparatus 10 relative to the principal analyte filter 30 such that selectively passed wavelengths emerging from the principal analyte filter interact with the second filter means, whereby the intensity of each passed wavelength is independently attenuated by the second filter means. The attenuations provided by the second filter means can be determined, for example, by an independent set of weighting factors derived using chemometrics techniques.

In one particular configuration, the weighting factors are determined using a partial least squares or principal component regression of an original spectrum obtained from a sample containing the analyte. The second filter means 32 can be constructed using a suitable substrate layer that is capable of transmitting radiation at least in the 600 to 3500 nm range. The substrate layer is generally coated with one or more layers of metals and/or oxides that are conventional in the art to provide a plurality of attenuating filter densities. Such coatings can be applied to the substrate using emulsion or chemical vapor deposition (CVD) techniques well known in the art. In an alternative apparatus, the second filter means is a photographic mask having spectral lines of optical density that are proportional to weighting functions determined using a rotated principal components or least squares analysis technique.

After attenuation by the second filter means, the independent wavelengths are communicated with a second detection means 34, such as a PbS detector or the like. As described above, the wavelengths emerging from the second filter means can be communicated to the second detection means via a focusing means 36, e.g., a collimating lens or the like. Alternatively, the apparatus 10 can include a radiation detector capable of directly receiving radiation from the second filter means.

The second detection means detects and converts the attenuated wavelengths emitted from the second filter means into a signal which can then be applied toward an analyte specific algorithm to determine analyte concentration. Specifically, signals obtained from the second detection means can be readily converted into digital signals using an analog/digital converter. The digitized information is readily available for input into a microprocessor where it is used to provide an analyte concentration which can be visualized on a display device and/or recorded on an output recorder.

The apparatus 10 can be used to obtain measurements of analyte concentration in a variety of complex media, such as in aqueous media having complex spectral backgrounds. In one application, the apparatus can be used in the determination of blood analyte concentrations, particularly organic blood analytes such as, but not limited to, glucose, urea (BUN), lipids, bilirubin and alcohol. The blood analyte can be present in an in vitro sample medium (e.g., a blood sample), or the apparatus can be used to measure blood analytes in tissue. However, the apparatus 10 is particularly adapted for use in field applications, e.g., in the measurement of blood alcohol, or in home health monitoring, e.g., in blood glucose determination.

Figure 2:
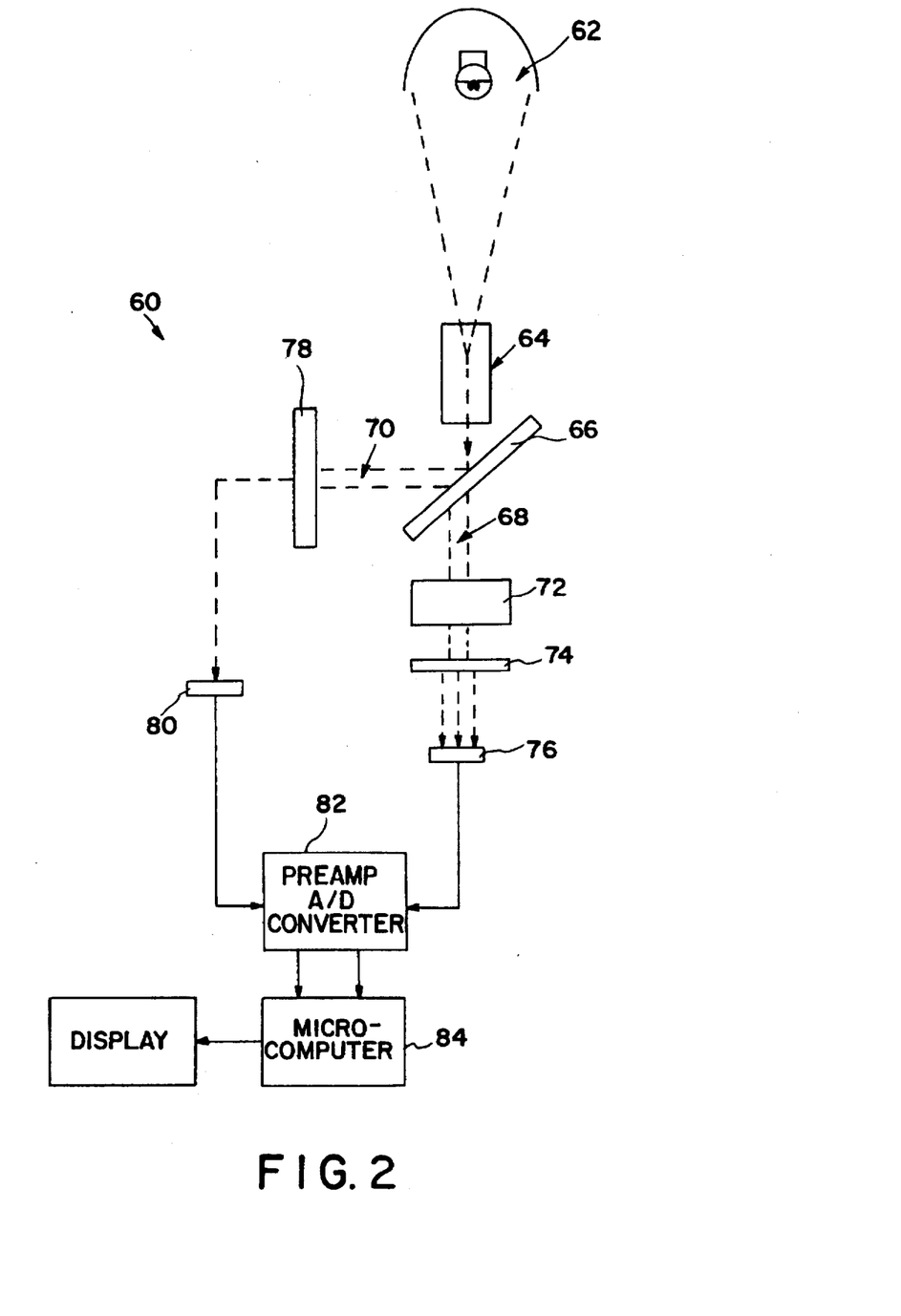
FIG. 2 is a diagrammatic representation of a correlation spectrometer apparatus constructed according to the invention.

Referring now to FIG. 2, an alternative apparatus for measurement of analyte concentration in a complex aqueous medium is generally indicated at 60. The apparatus includes a radiation source 62 which provides a plurality of distinct, nonoverlapping regions of wavelengths in the approximate range of 600 to approximately 3500 nm. Radiation from source 62 is transmitted to an optically active means 64 for receiving and directing the radiation into a beam path and/or for passing selected wavelengths, such as a collimating lens, selective filtering means or the like.

Near-IR radiation emerging from means 64 is communicated through a beam splitter 66, whereby the radiation is divided into two beams, respectively indicated at 68 and 70. The first beam 68 from beam splitter 66 is transmitted to a sample medium 72 containing an unknown concentration of an analyte of interest. In FIG. 2, the sample medium 72 comprises a sample cell formed from a suitable substrate capable of transmitting radiation in the near-IR range of interest. In one case, the sample can comprise a blood serum sample, wherein it is desired to determine the concentration of blood analytes. Alternatively, the first beam 68 can be transmitted to a sample surface such as a tissue surface using direct interfacing means or indirect interfacing means, e.g., fiber optic waveguides means such as those described supra. In this manner, the concentration of blood analytes present in the tissue sample can be non-invasively determined using reflective near-IR measurement of the absorption spectrum of radiation which has interacted with the tissue sample.

Radiation, including the spectrally modified radiation that has interacted with the constituents of the sample, e.g., the analyte of interest, is then collected and directed to an optical transfer cell 74 which is disposed in the beam path. The optical transfer cell 74 comprises a positive correlation filter system having an absorption spectrum sufficient to accept the radiation and selectively emphasize one or more wavelengths therefrom having high correlation with the concentration of an analyte of interest, and substantially no correlation with interfering components present in the sample. The positive correlation filter system thus passes a population of selected wavelength ranges which provide analyte-specific information, as well as information about the measurement background and information that can be used to correct for instrument changes or interference effects. Radiation emerging from the optical transfer cell 74 is received by a detection means 76 for converting the spectrally modified radiation into a signal that is representative of the intensity of that radiation. The detection means can comprise a broad spectrum photodetector such as an PbS photodetector or the like.

Referring still to FIG. 2, the second beam 70 from beam splitter 66 is transmitted to an optically active element 78 which is disposed in the beam path. In one configuration, the optically active element 78 comprises a neutral density filter means having absorption characteristics sufficient to attenuate radiation equally over a selected range of near-IR wavelengths. In an alternative configuration, the optically active element 78 is an optical transfer cell that includes a positive correlation filter system having an absorption spectrum that is identical to the absorption spectrum of optical transfer cell element 74. The radiation emerging from the optically active element 78 is received by a detection means 80 for converting the radiation into signals representative of the intensity thereof.

The positive correlation filter systems can be formed from a single substrate layer having an optically active coating which imparts absorption characteristics capable of selectively emphasizing one or more wavelengths having high correlation with a particular analyte concentration. In particular system configurations, the positive correlation filter comprises a plurality of filter layers, each layer having a selected filter density and/or filter thickness suitable to provide a desired absorption characteristic. In one case, at least one layer of the system has a filter density and/or thickness that comprises a wavelength weighting factor means, wherein the weighting factor provides enhanced positive correlation of a passed wavelength with the concentration of an analyte in the selected sample medium.

The signals generated by detection means 76 and 80 are then communicated to a means 82 for converting those signals into a digital signal indicative of the ratio of the intensity of the radiation emerging from the source 62 and the corresponding spectrally modified radiation emerging from the sample. In this manner, changes in the intensity of the radiation emerging from the source 62 can be corrected for, eliminating a potential source of error in the measurement obtained from the system. Further, the ratio of the signals can then be converted to digital form and interpreted to determine analyte concentration using an internal microprocessor 84 system or an associated system using methods known in the art.

If desired, the microprocessor can be programmed to calculate analyte concentration by application of a chemometrics algorithm to the ratio signal. The appropriate algorithm can be determined using the above-described chemometrics techniques, such as a least squares analysis or rotated principal component analysis of an original absorption spectrum of the analyte of interest.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE

A noninvasive glucose measurement was obtained using the method of the invention. Particularly, reflective optical measurements in the near-IR region of approximately 1100 nm to 3500 nm were carried out. Spectral scans were collected from volunteer forearm subjects, using an instrument having a Tungsten-Mercury (W-Hg) radiation source, a Lead Sulfide (PbS) detector and a scan speed of nm/0.4 second.

Figure 3:
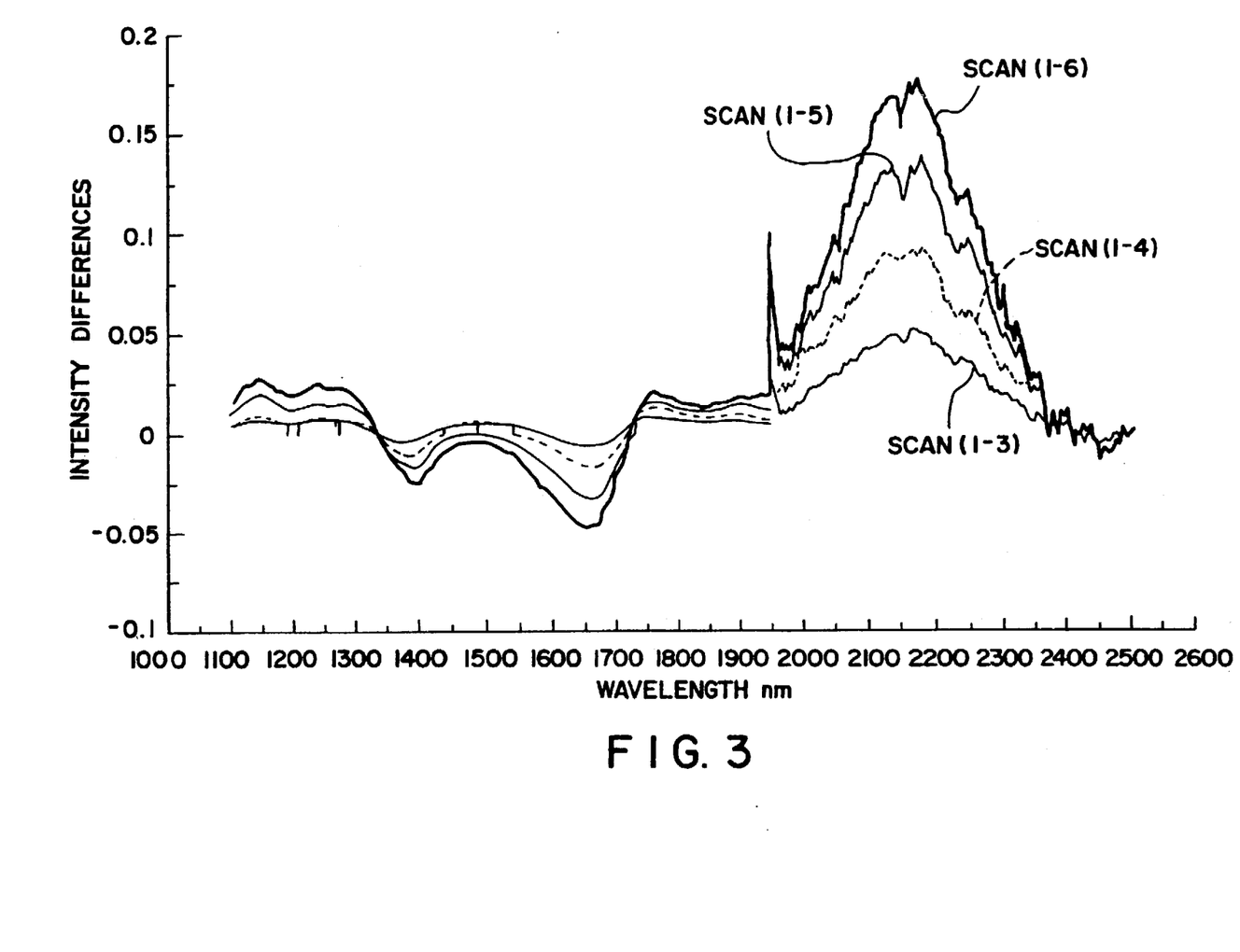
FIG. 3 is a graph illustrating time-dependent scans taken during an in vivo glucose tolerance study.

A number of specific spectral ranges were identified as containing information which can be used to determine glucose concentration from a forearm tissue scan. The specified regions were determined from an in vivo glucose tolerance study conducted in tandem with invasively-obtained in vitro blood glucose concentration determinations. In particular, time-dependent scans taken during the in vivo tolerance study are depicted in FIG. 3. As can be seen, significant changes in the reflective intensity differences over the range of about 2120 to 2180 nm were recorded during the time course of the study. These changes increased in direct relation to increases in blood glucose level during the tolerance test, signifying that the range of 2120 to 2180 nm contains glucose-specific spectral information.

Once the specific spectral ranges were identified, noninvasive glucose measurements were obtained using information from the four distinct spectral ranges. The first spectral range included radiation occurring at about 1320 to 1340 nm. This range provides a very highly reflected signal, and there is no major glucose absorption band in this range. Information obtained from the first spectral range can be used to normalize each individual scan in order to correct for fluctuations in the radiation source, and changes due to mechanical perturbations.

The second spectral range included radiation occurring at either about 1440 to 1460 nm, or about 1940 to 1960 nm. These ranges provide a substantially nonreflected signal due to the highly absorptive water bands which attenuate diffusively reflected radiation. Information obtained from these ranges can be used for background and base line subtraction from other measurements. These measurements allow for a pedestal adjustment to account for fluctuations induced by specular reflection signal values, and can be used to detect improper measurements.

The third range included radiation occurring at about 1670 to 1690 nm. This range provides analyte-specific information due to the presence of glucose vibrational overtone bands.

The fourth range included radiation occurring at about 2120 to 2280 nm. This range provides analyte-specific information due to glucose combination vibrational bands.

Signals obtained from the first range were used to normalize signals of other regions. This process, when repeated with each spectral scan, eliminates the problem associated with light source changes and serves to provide an internal reference. Measurement variations induced by differences in optical interface, e.g., patient placements, were accordingly substantially reduced.

Background information was eliminated by subtracting the signals obtained in the second range, from the signals obtained in the third and fourth analyte-specific ranges. In this manner, the pedestal effect created by specular reflection, which varies with skin texture and age, was corrected for.

Figure 4:
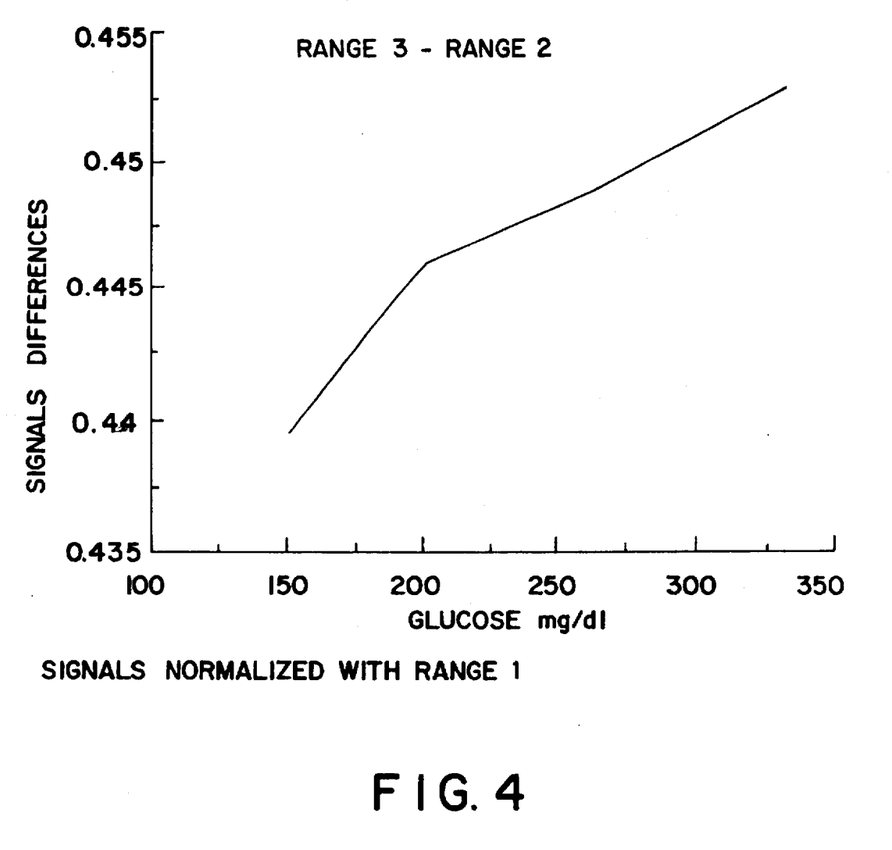
FIG. 4 depicts in graph form the results obtained from a noninvasive determination of blood glucose concentration conducted using the method of the invention.

The normalized and base line corrected signals from the third and fourth ranges were applied in an analytical chemometric analysis. FIG. 4 depicts the normalized differences between signals in the second and third ranges.

As can be seen by the results depicted in FIG. 4, increase in blood glucose level results in an increase in the signal differences between the two ranges.

We claim:

1. An apparatus for determining the concentration of an analyte in a sample, comprising:
   (a) means for irradiating the sample with incident radiation containing a plurality of distinct, nonoverlapping regions of wavelengths in the range of approximately 1100 to 3500 nm;
   (b) means for collecting reflected radiation emerging from the sample and directing said reflected radiation into first and second light paths, wherein the first light path comprises radiation from a first region of wavelengths;
   (c) first filter means disposed in the first light path, wherein the first filter means is capable of selectively passing radiation having substantially no correlation with the concentration of the analyte;
   (d) first detection means for receiving selectively passed radiation emerging from the first filter means, and means for converting the same into a signal representative of the intensity of said radiation;
   (e) adjustable filter means disposed in the second light path, wherein the adjustable filter means attenuates the intensity of radiation in the second light path;
   (f) principal analyte filter means capable of receiving attenuated radiation emerging from the adjustable filter means, and selectively passing one or more independent wavelengths therefrom, wherein the said one or more independent wavelengths are specifically correlated with the concentration of the analyte;
   (g) second filter means capable of receiving the one or more independent wavelengths emerging from the principal analyte filter means and attenuating the intensity of each independent wavelength;
   (h) second detection means for receiving the attenuated independent wavelengths emerging from the second filter means; and
   (i) means for converting the detected wavelengths into a signal representative of the intensity of said wavelengths.

2. The apparatus of claim 1, wherein the first filter means comprises a narrow band-pass filter.

3. The apparatus of claim 2, wherein the adjustable filter means comprises a neutral density filter used in concert with correlation filters in a filter system.

4. The apparatus of claim 3, wherein the signal obtained from the first detection means is used to regulate attenuation provided by the adjustable filter means.

5. The apparatus of claim 1, wherein the second filter means comprises a neutral density filter used in concert with correlation filters in a filter system.

6. The apparatus of claim 5, wherein the attenuation provided by the second filter means is established using weighting factors.

7. The apparatus of claim 6, wherein the weighting factors are derived using chemometrics techniques.

8. The apparatus of claim 7, wherein the weighting factors are derived using rotated principal components analysis of an absorption spectrum of the analyte.

9. The apparatus of claim 1, wherein the sample comprises body tissue and the analyte comprises an organic blood analyte.

10. The apparatus of claim 9, wherein the blood analyte is selected from the group consisting of glucose, urea (BUN), lipids, bilirubin and ethyl alcohol.

11. The apparatus of claim 9, wherein the blood analyte is glucose.

12. An apparatus for determining the concentration of an analyte in a sample, comprising:
 (a) a source capable of emitting near infrared radiation containing a plurality of distinct, nonoverlapping regions of wavelength in the range of approximately 1100 to 3500 nm;
 (b) means for dividing radiation emerging from the source of part (a) into first and second beam paths;
 (c) means for irradiating the sample with the radiation in the first beam path, thereby providing reflected radiation;
 (d) means for collecting the reflected radiation emerging from the sample and directing said reflected radiation into a reflected light path;
 (e) a first optical transfer cell disposed in the reflected light path, said first cell comprising first positive correlation filter means having absorption characteristics adapted to accept the reflected radiation and emphasize one or more wavelengths from the reflected radiation, wherein said one or more wavelengths have high correlation with the concentration of the analyte in the sample;
 (f) means for receiving the one or more emphasized wavelengths from the first optical transfer cell and for converting the same into signals representative of the intensity of said emphasized wavelengths;
 (g) a second optical transfer cell disposed in the second beam path, said second cell comprising neutral density filter means having absorption characteristics sufficient to attenuate the intensity of the radiation from the second beam path equally over a selected range of near infrared wavelengths;
 (h) means for receiving attenuated radiation from the second optical transfer cell and for converting the same into signals representative of the intensity thereof; and
 (i) means for calculating the concentration of the analyte in the sample using the signals generated by parts (f) and (h).

13. The apparatus of claim 12, wherein the means for calculating the concentration of the analyte in the sample converts the signals generated by parts (f) and (h) into a digital signal indicative of the ratio of the intensity of the radiation emerging from the source and corresponding radiation emerging from the sample.

14. The apparatus of claim 12, wherein the means for calculating the concentration of analyte in the sample comprises means for applying a chemometrics algorithm to the signals generated by parts (f) and (h).

15. The apparatus of claim 12, wherein the first positive correlation filter means comprises a plurality of layers, each layer having selected absorption characteristics such that said filter means emphasizes a population of wavelengths having high correlation with the analyte concentration.

16. The apparatus of claim 12, wherein the sample comprises body tissue and the analyte comprises an organic blood analyte.

17. The apparatus of claim 16, wherein the blood analyte is selected from the group consisting of glucose, urea (BUN), lipids, bilirubin and ethyl alcohol.

18. The apparatus of claim 16, wherein the blood analyte is glucose.

19. An apparatus for determining the concentration of an analyte in a sample, comprising:
 (a) a source capable of emitting near infrared radiation containing a plurality of distinct, nonoverlapping regions of wavelength in the range of approximately 1100 to 3500 nm;
 (b) means for dividing radiation emerging from the source of part (a) into first and second beam paths;
 (c) means for irradiating the sample with the radiation in the first beam path, thereby providing reflected radiation;
 (d) means for collecting the reflected radiation emerging from the sample and directing said reflected radiation into a reflected light path;
 (e) a first optical transfer cell disposed in the reflected light path, said first cell comprising first positive correlation filter means having absorption characteristics adapted to accept the reflected radiation and emphasize one or more wavelengths from the reflected radiation, wherein said one or more wavelengths have high correlation with the concentration of the analyte in the sample;
 (f) means for receiving the one or more emphasized wavelengths from the first optical transfer cell and for converting the same into signals representative of the intensity of said emphasized wavelengths;
 (g) a second optical transfer cell disposed in the second beam path, said second cell comprising a second positive correlation filter means having absorption characteristics identical to those of the first positive correlation filter means;
 (h) means for receiving attenuated radiation from the second optical transfer cell and for converting the same into signals representative of the intensity thereof; and
 (i) means for calculating the concentration of the analyte in the sample using the signals generated by parts (f) and (h).

20. The apparatus of claim 19, wherein the first positive correlation filter means comprises a plurality of layers, each layer having selected absorption characteristics such that said filter means emphasizes a population of wavelengths having high correlation with the analyte concentration.

21. The apparatus of claim 20, wherein the absorption characteristics of at least one layer from the first and second positive correlation filter means are established using weighting factors.

22. The apparatus of claim 21, wherein the weighting factors are derived using chemometrics techniques.

23. The apparatus of claim 22, wherein the weighting factors are derived using rotated principal components analysis of an absorption spectrum of the analyte.

* * * * *